United States Patent
Kim et al.

(10) Patent No.: US 12,223,568 B2
(45) Date of Patent: Feb. 11, 2025

(54) SYSTEMS AND METHODS FOR GENERATING AND ESTIMATING UNKNOWN AND UNACQUIRED ULTRASOUND DATA

(71) Applicant: Mayo Foundation for Medical Education and Research, Rochester, MN (US)

(72) Inventors: Bae-Hyung Kim, London (GB); Azra Alizad, Rochester, MN (US); Mostafa Fatemi, Rochester, MN (US); Viksit Kumar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 675 days.

(21) Appl. No.: 17/257,936

(22) PCT Filed: Jul. 8, 2019

(86) PCT No.: PCT/US2019/040806
§ 371 (c)(1),
(2) Date: Jan. 5, 2021

(87) PCT Pub. No.: WO2020/010351
PCT Pub. Date: Jan. 9, 2020

(65) Prior Publication Data
US 2021/0272339 A1 Sep. 2, 2021

Related U.S. Application Data

(60) Provisional application No. 62/694,842, filed on Jul. 6, 2018.

(51) Int. Cl.
*G06K 9/00* (2022.01)
*A61B 8/00* (2006.01)
(Continued)

(52) U.S. Cl.
CPC .......... *G06T 11/008* (2013.01); *A61B 8/4245* (2013.01); *G06N 20/00* (2019.01); *G06N 3/08* (2013.01)

(58) Field of Classification Search
CPC . G06T 2207/20081; G06T 2207/20084; G06T 2207/10132; G06T 7/0012;
(Continued)

(56) References Cited

U.S. PATENT DOCUMENTS

| 5,537,367 A | 7/1996 | Lockwood |
| 6,224,556 B1 | 5/2001 | Schwartz |

(Continued)

OTHER PUBLICATIONS

Hu, Freehand Ultrasound Image Simulation with Spatially-Conditioned Generative Adversarial Networks, Sep. 9, 2017, Springer (Year: 2017).*

(Continued)

*Primary Examiner* — Alex Kok S Liew
(74) *Attorney, Agent, or Firm* — Quarles & Brady LLP (57) ABSTRACT

Systems and methods for reconstructing, estimating, or otherwise generating unacquired, undetected, unreconstructed, or otherwise unknown ultrasound data using machine learning algorithms are provided. Thus, the systems and methods described in the present disclosure provide for generating unacquired, undetected, unreconstructed, or otherwise unknown data that are not actually and physically acquired with an ultrasound transducer and/or front-end receiver of an ultrasound system.

15 Claims, 9 Drawing Sheets

(51) Int. Cl.
  *G06N 20/00* (2019.01)
  *G06T 11/00* (2006.01)
  *G06N 3/08* (2023.01)
(58) Field of Classification Search
  CPC . G06T 2207/10088; G06T 2207/30096; G06T 2207/10081; G06T 7/0014; G06T 2207/10136; G06T 2207/10104; G06T 2207/10116; G06T 2207/30008; G06T 2207/30016; G06T 2207/30048; G06T 7/344; G06T 11/008; G06T 2207/10016; G06T 7/0016; G06T 7/30; G06T 11/006; G06T 13/20; G06T 15/205; G06T 2200/08; G06T 2207/20004; G06T 5/50; G06T 7/11; G06T 7/12; G06T 11/00; G06N 3/045; G06N 3/08; G06N 3/047; G06N 3/088; G06N 3/084; G06N 3/04; G06N 20/00; G06N 3/048
  See application file for complete search history.

(56) References Cited

U.S. PATENT DOCUMENTS

| 7,826,308 | B2 | 11/2010 | Song | |
|---|---|---|---|---|
| 2016/0113630 | A1 | 4/2016 | Chang | |
| 2016/0209502 | A1 | 7/2016 | Kim | |
| 2019/0295295 | A1* | 9/2019 | Hyun | A61B 8/5215 |

OTHER PUBLICATIONS

K. He, X. Zhang, S. Ren and J. Sun, "Deep Residual Learning for Image Recognition," 2016 IEEE Conference on Computer Vision and Pattern Recognition (CVPR), Las Vegas, NV, USA, 2016, pp. 770-778 (Year: 2016).*
Austeng A. et al.: '1D and 2D algorithmically optimized sparse arrays', IEEE Ultrason. Symp., Toronto, Canada, Oct. 1997, pp. 1683-1686.
Greenspan, H. et al "Deep Learning in Medical Imaging: Overview and Future Promise of an Exciting New Technique," IEEE Transactions on Medical Imaging, 2016, vol. 35, No. 5, pp. 1153-1159.
International Searching Authority. International Search Report and Written Opinion for application PCT/US2019/040806. Mailed on Jul. 8, 2019. 15 pages.
Jensen, J. et al, "Optimized plane wave imaging for fast and high-quality ultrasound imaging," IEEE transactions on ultrasonics, ferroelectrics, and frequency control, vol. 63, pp. 1922-1934, 2016.
Karamen M. et al.: 'Minimally redundant 2-D array designs for 3-D medical ultrasound imaging', IEEE Trans. Med. Imaging, 2009, 28, 7, pp. 1051-1061.
Kim, B.H et al.: 'Design and Test of a Fully Controllable 64x128 2-D CMUT Array Integrated with Reconfigurable Frontend ASICs for Volumetric Ultrasound Imaging', IEEE Ultrason. Symp., Dresden, Germany, Oct. 2012, pp. 77-80.
Klebaek, H. et al. "Neural network for sonogram gap filling." 1995 IEEE Ultrasonics Symposium. Proceedings. An International Symposium. vol. 2. IEEE, 1995.
Liebgott, H. et al, "Pre-beamformed RF signal reconstruction in medical ultrasound using compressive sensing," Ultrasonics 53.2 (2013): 525-533.
Lockwood G.R. et al.: 'Optimizing the radiation pattern of sparse periodic linear arrays'. IEEE Trans. Ultrason. Ferroelectr. Freq Control, 1996, 43, 1, pp. 7-14.
Looney P. et al., "Automatic 3D ultrasound segmentation of the first trimester placenta using deep learning," Biomedical Imaging (ISBI 2017), 2017 IEEE 14th International Symposium on, Apr. 2017.
Lorintiu, O. et al, "Compressed Sensing Reconstruction of 3D Ultrasound Data Using Dictionary Learning and Line-Wise Subsampling," IEEE Transactions on Medical Imaging, 2015, vol. 34, No. 12, pp. 2467-2477.
Luchies, A. C., et al. "Deep neural networks for ultrasound beamforming." IEEE transactions on medical imaging 37.9 (2018): 2010-2021.
Perdios D. et al., "A deep learning approach to ultrasound image recovery," Ultrasonics Symposium (IUS), 2017 IEEE International, Washington DC., USA, Sep. 2017.
Rodriguez-Molares, A. et al, "Axial lobes in coherent plane-wave compounding," in Ultrasonics Symposium (IUS), 2016 IEEE International, 2016, pp. 1-4.
Sahiner B. et al., "Classification of mass and normal breasttissue: A convolution neural network classifier with spatial domain and texture images," IEEE Trans. Med. Imag., vol. 15, No. 5, pp. 598-610, Oct. 1996.
Schraudolph, N. N., et al. "Temporal difference learning of position evaluation in the game of Go." Advances in Neural Information Processing Systems (1994): 817-817.
Shattuck, D.P. et al, "Explososcan: A parallel processing technique for high speed ultrasound imaging with linear phased arrays," Journal of the Acoustical Society of America, vol. 75, pp. 1273-1282, 1984.
Siemens Healthineers. ACUSON SC2000 PRIME Ultrasound System. Webpage. Version accessed Sep. 29, 2020. Available online at https://web.archive.org/web/20200929130250if_/https://www.siemens-healthineers.com/ultrasound/cardiovascular/acuson-sc2000-ultrasound-system#FEATURES_BENEFITS.
Silver, D. et al. "Mastering the game of Go with deep neural networks and tree search". Nature, 529(7587): 484-489. 2016.
Silver, D. et al. Google AI Blog: AlphaGo: Mastering the ancient game of Go with Machine Learning. Google Research Blog. Jan. 27, 2016. Available online at https://ai.googleblog.com/2016/01/alphago-mastering-ancient-game-of-go.html.
Turnbull D.H. et al.: 'Beam steering with pulsed two-dimensional transducer arrays', IEEE Trans. Ultrason. Ferroelectr. Freq Control, 1991, 38, 4, pp. 320-333.
Wagner, N. et al, "Compressed beamforming in ultrasound imaging," IEEE Trans. Signal Process., vol. 60, No. 9, pp. 4643-4657, 2012.
Wang, H., et al. "Breast mass classification via deeply integrating the contextual information from multi-view data." Pattern Recognition 80 (2018): 42-52.
Wikipedia, AlphaGo, Version dated Jul. 5, 2018. Available online at https://web.archive.org/web/20180705102456/ https://en.wikipedia.org/wiki/AlphaGo.
Yoon, Y. H., et al. "Deep Learning for Accelerated Ultrasound Imaging." arXiv preprint arXiv:1710.10006 (2017).
Yoon, Y. H., et al. "Deep learning in rf sub-sampled b-mode ultrasound imaging." arXiv preprint arXiv:1712.06096 (2017).

* cited by examiner

SYSTEMS AND METHODS FOR GENERATING AND ESTIMATING UNKNOWN AND UNACQUIRED ULTRASOUND DATA

CROSS-REFERENCE TO RELATED APPLICATIONS

This application is a 371 U.S. National Phase application of PCT/US2019/040806, filed Jul. 8, 2019, which claims the benefit of U.S. Provisional Patent Application Ser. No. 62/694,842, filed on Jul. 6, 2018, and entitled "SYSTEMS AND METHODS FOR GENERATING AND ESTIMATING UNKNOWN AND UNACQUIRED ULTRASOUND DATA," which is herein incorporated by reference in its entirety.

STATEMENT REGARDING FEDERALLY SPONSORED RESEARCH

This invention was made with government support under CA148994, CA195527, and CA174723 awarded by the National Institutes of Health. The government has certain rights in the invention.

BACKGROUND

In medical ultrasound imaging systems, a number of channel data is used for reconstructing ultrasound images and for demonstrating diagnostic information. Lowering the number of channels reduces the size and cost of the ultrasound system, but also results in lower ultrasound imaging quality. Sparse array techniques can be used to reduce the number of system channels; however, these techniques introduce artifacts, such as grating lobes, due to the sparsity of the source apertures and these artifacts degrade the image quality.

SUMMARY OF THE DISCLOSURE

The present disclosure addresses the aforementioned drawbacks by providing a method for reconstructing an image from data acquired with an ultrasound system. The method includes accessing with a computer system, ultrasound data acquired from a subject with an ultrasound system. Additional ultrasound data are generated with the computer system by inputting the ultrasound data to a trained machine learning algorithm that is trained to generate additional ultrasound data based on the acquired ultrasound data, generating output as the additional ultrasound data. An image is reconstructed from the ultrasound data and the additional ultrasound data using the computer system. The image depicts the subject from which the ultrasound data were acquired.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for reconstructing, estimating, or otherwise generating unacquired, undetected, unreconstructed, or otherwise unknown ultrasound data using machine learning algorithms implemented with a hardware processor and memory. Thus, the systems and methods described in the present disclosure provide for generating unacquired, undetected, unreconstructed, or otherwise unknown data that are not actually and physically acquired with an ultrasound transducer and/or front-end receiver of an ultrasound system.

By generating more data from which images can be reconstructed, the systems and methods described in the present disclosure enable direct improvement of image quality (e.g., increased resolution, better contrast-to-noise ratio ("CNR"), reduced artifacts) without assigning the information to an unacquired data channel. The methods can be implemented for any suitable ultrasound imaging application, including Doppler imaging, and other acoustic imaging modalities, including acoustic microscopy; nondestructive testing and evaluation of materials; underwater and sonar imaging; and photoacoustic imaging. The methods can also be adapted for use in other imaging modalities, such as magnetic resonance imaging, computed tomography, positron emission tomography, and optical imaging, as well as other applications such as radar. In each of these instances, unacquired data are generated from input data that have been acquired or otherwise estimated.

These unacquired data can be viewed as data from one or more "virtual channels." In some implementations, the virtual channel data can be associated with physical channels from which data are not otherwise acquired. The virtual channel data can be associated with any arbitrary position of transducer. For instance, the virtual channel data can be data associated with an arbitrary position of a two-dimensional array transducer, circular array transducer, or any other suitable type of transducer. In this way, a "virtual transducer" that is not actually used for transmission and reception in the imaging system can be established and used. Using the systems and methods described in the present disclosure, a signal for any position in the virtual transducer can be generated, even if it is not used in an actual imaging scan or data acquisition.

By estimating virtual channel data the active number of channels in an ultrasound system can be reduced. In this way, images can be reconstructed using only a few channels of actually acquired data. As such, the images are reconstructed using only a few channels of acquired data.

In accordance with some embodiments of the systems and methods described in the present disclosure, a trained machine learning algorithm implemented with a hardware processor and a memory can be used to generate additional ultrasound data from input ultrasound data. For example, in some embodiments, the additional ultrasound data (e.g., virtual channel data) can correspond to data associated with empty channels, inactive channels, unacquired angles (e.g., in compounded imaging applications), and so on. In some implementations, the additional ultrasound data can be input to the trained machine learning algorithm in order to generate still more additional ultrasound data (e.g., virtual channel data). In this way, the trained machine learning algorithm can take as inputs both ultrasound data and virtual channel data, and can be implemented in a recursive or iterative manner in order to generate a desired amount of additional ultrasound data.

Additionally or alternatively, additional ultrasound data can be estimated or otherwise generated by inputting the ultrasound data to a suitable signal processing technique, such as interpolation and estimation/prediction, generating output as additional ultrasound data. As one example, the ultrasound data can be input to a time-space signal interpolation algorithm that is based on the interpolation of spatial sampling in k-space domain in order to generate output as the additional ultrasound data.

The systems and methods described in the present disclosure are capable of reconstructing an image from $L_s$ ($1 \leq L_S < L$) channels, where the reconstructed image is comparable with an image reconstructed from beamformed data using L channels. As an example, an image can be reconstructed and beamformed using 1 channel, where the resulting image has image quality similar to, or better than, an image reconstructed from 64 or 128 channel data, without requiring increased complexity and significant change in hardware or front-end architecture.

Figure 1:
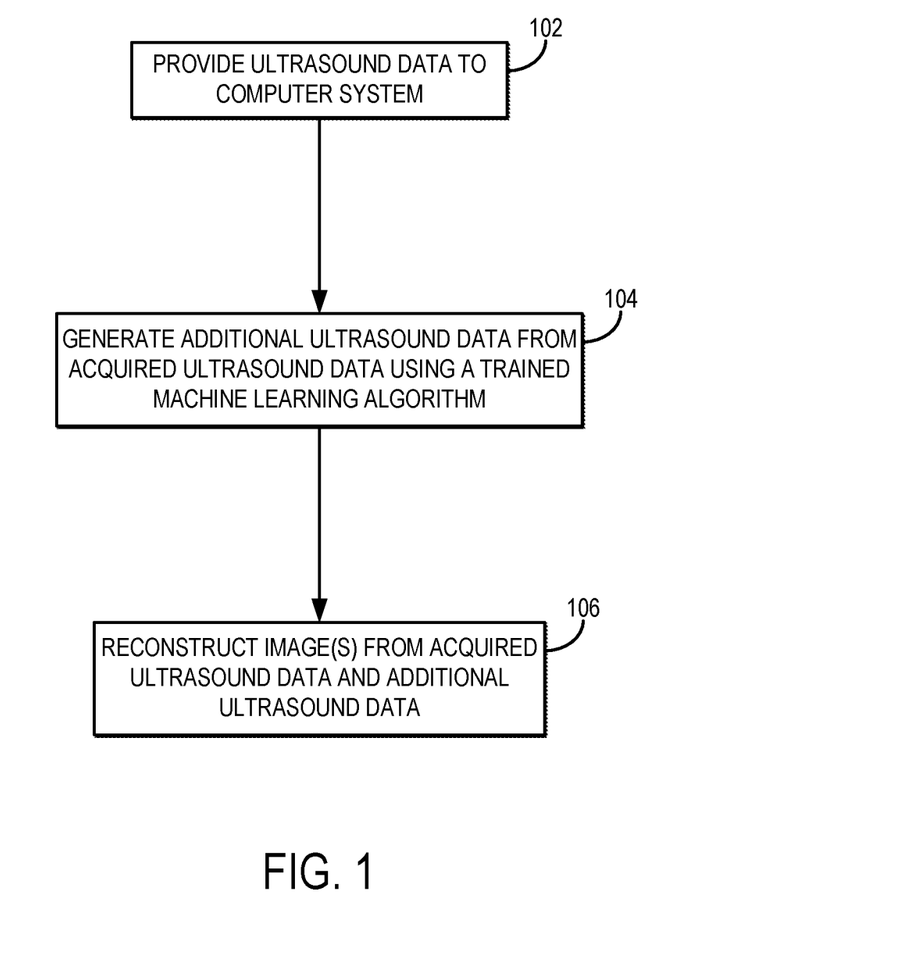
FIG. 1 is a flowchart setting forth the steps of an example method for generating additional ultrasound data from initially acquired ultrasound data using an appropriately trained machine learning algorithm implemented with a hardware processor and a memory, and for reconstructing image(s) from such data.

Referring now to FIG. 1, a flowchart is illustrated as setting forth the steps of an example method for generating additional ultrasound data using a trained machine learning algorithm implemented with a hardware processor and memory.

The method includes providing ultrasound data to a computer system, as indicated at step 102. The ultrasound data can include data or data sets from one or more points in an ultrasound signal processing chain for reconstructing ultrasound images. For example, the ultrasound data can include radio frequency ("RF") echo channel data, RF beamformed data, in-phase and quadrature ("I/Q") data, envelope detected data, image pixel data, and so on. The ultrasound data can be provided to the computer system by accessing previously acquired ultrasound data from a memory or data storage, or by acquiring ultrasound data with an ultrasound system and providing the acquired ultrasound data to a computer system, which may be a part of the ultrasound system.

In general, the acquired ultrasound data include fewer data than desirable for reconstructing a high quality image. The systems and methods described in the present disclosure are thus used to generate additional ultrasound data from the acquired ultrasound data, such that a higher quality image can be reconstructed from the collective acquired and additional ultrasound data.

The method thus includes providing the acquired ultrasound data to a trained machine learning algorithm implemented with a hardware processor and memory of the computer system in order to generate additional ultrasound data, as indicated at step 104. One or more images can then be reconstructed from the acquired ultrasound data and the additional ultrasound data, as indicated at step 106.

The trained machine learning algorithm can be any suitable artificial intelligence algorithm that has been trained for generating additional ultrasound data from input data that includes acquired ultrasound data, and in some instances acquired ultrasound data and additional information or data useful for estimating the additional ultrasound data. Artificial intelligence can be broadly divided into rule based systems, classical machine learning, and representation learning. Classical machine learning can include both supervised and unsupervised learning based algorithms. Representation learning algorithms are based on extracted features, which can include dictionary based features or features generated with auto feature generation using deep learning. Deep learning can be further subdivided into convolution neural networks ("CNN"), recurrent neural networks ("RNN"), deep neural networks ("DNN"), and so on.

In some embodiments, the additional ultrasound data generated by the trained machine learning algorithm correspond to empty or inactivated channels. An empty channel can result from a designed array aperture shape (e.g., a sparse array) or from broken transducer elements or electronics. An inactivated channel can be an inactive channel among transducer elements, or a gap between actually designed array elements. In general, the technique for generating and estimating data of an empty or inactivated channel for beamforming is called gap-filling ("GF") or gap-interpolation ("GI"). GF techniques can include using neighboring data acquired in an active channel, which utilizes known and/or given information for gap filling; using additional information for gap filling; and using both given and additional information for gap filling.

For generating and estimating new data from actually acquired and known data, linear or non-linear prediction methods can be used, such as, $$x_j(n) = a_i x_i(l) + a_k x_k(m) \quad (1);$$

$$x_j(n) = f(x_1(k), \ldots, x_i(l), \ldots, x_L(m)) \quad (2);$$

$$x_j(n) = f(x_1(n), \ldots, x_i(n), \ldots, x_L(n)) \quad (3);$$

where $x_j(n)$ is a virtually generated nth sample of known data in the jth data set; $x_i(n)$ and $x_k(n)$ are the nth samples of actually acquired or reconstructed data in the ith and kth data sets, respectively; $a_i$ and $a_k$ are the gain for the linear prediction, respectively; $x_1(n)$ is the nth sample of actually acquired or reconstructed data in a first data set; $x_N(n)$ is the nth sample of actually acquired or reconstructed data in the Nth active channel; and $f(\cdot)$ is a function for the prediction.

Neighboring channel data can be used for the estimation or prediction to create empty or unknown channel data. Neighboring beamformed data can be utilized for creating a new beamformed line by using the existing and known beamformed lines. I/Q data already given by demodulation processing can be used for generating new I/Q data in the spatial and temporal domains. Pixel data for ultrasound imaging that are not actually reconstructed can be virtually generated with the data, which are already reconstructed and known.

Figure 2:
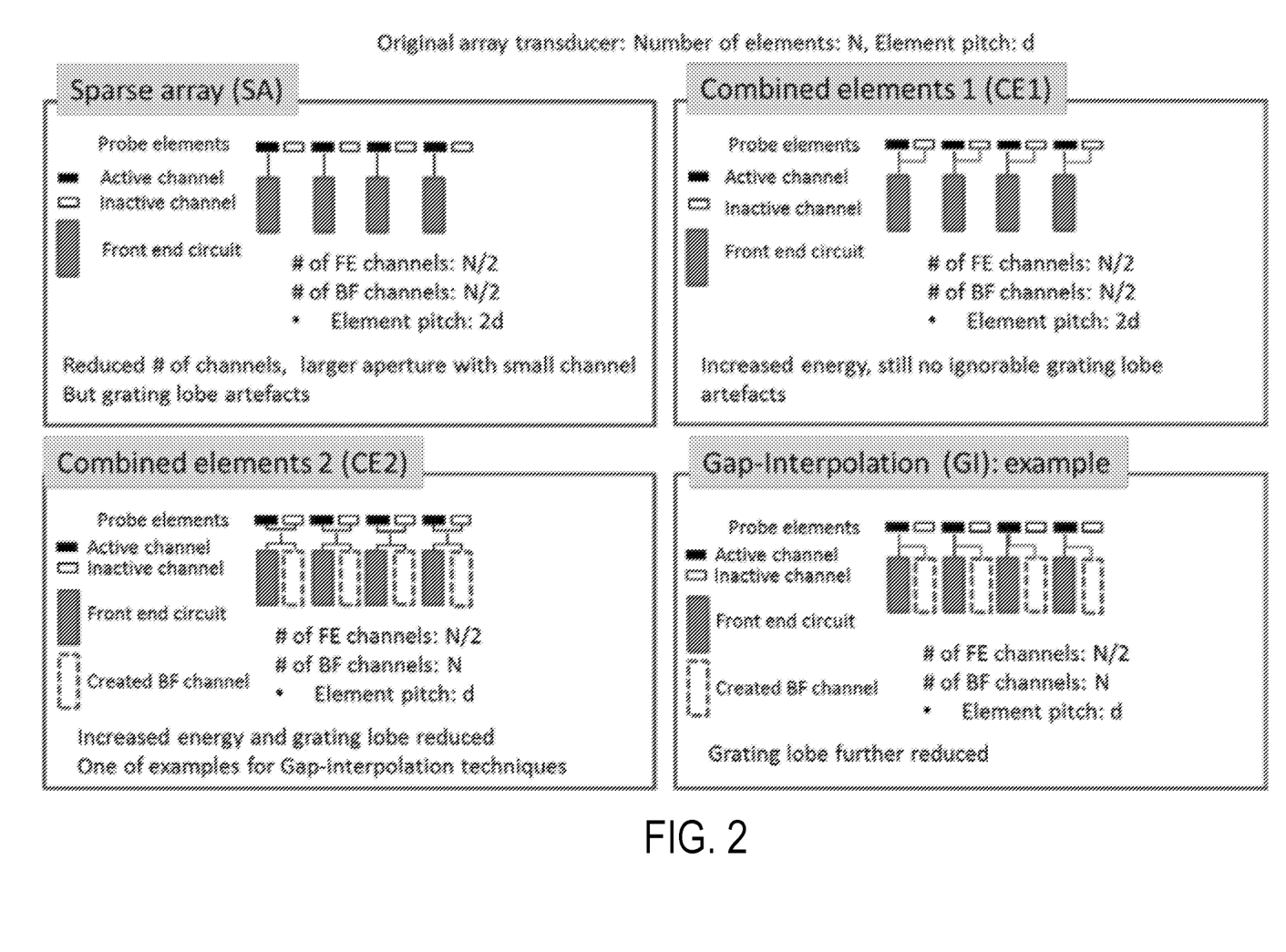
FIG. 2 is an example illustration of sparse array, combined element, and gap interpolation techniques.

FIG. 2 shows an example illustration of sparse array ("SA") and gap interpolation techniques. SA techniques (top left) use inactive elements, which can reduce the number of active channels. A first combined elements ("CE1") technique (top right) uses combined elements to reduce the number of channels, but with these techniques grating lobe artifacts may still be present. A second combined elements ("CE2") technique (bottom left) uses interpolated data as inactive channel data for beamforming to suppress the gating lobe artifacts. GI techniques (bottom right) use an alternative interpolation method to generate additional channel data associated with inactive elements for beamforming.

Figure 3:
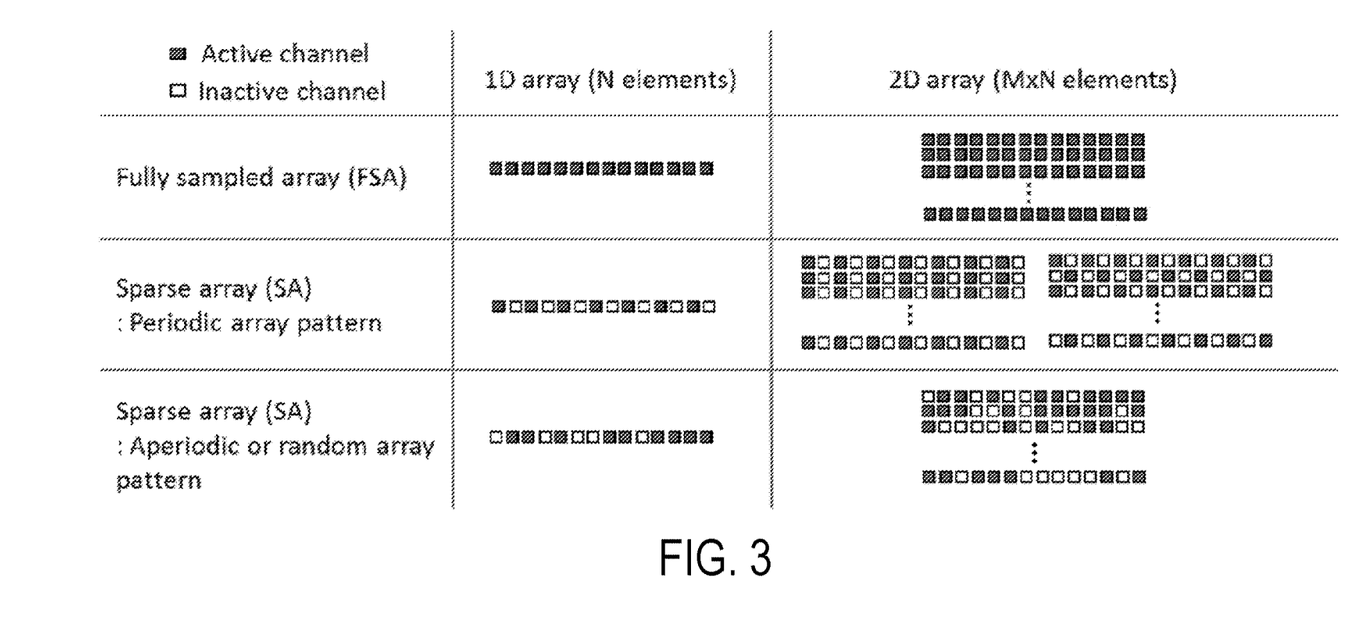
FIG. 3 shows an example classification for sparse array techniques for 1D and 2D array elements.

One example of an array aperture type used in ultrasound systems is a fully sampled array ("FSA"), which does not use any sparsity in its transmit ("Tx") or receive ("Rx") channels. In the viewpoint of beamforming, if there is any difference between inter-element spacing (i.e., pitch) in the array transducer and the inter-channel spacing in the Tx or Rx beamformer, the array transducer can be referred to as a non-fully sampled array ("NFSA") or sparse array ("SA"). Sparse arrays can be classified as periodic or aperiodic. FIG. 3 shows examples of different classifications for SA techniques in 1D and 2D arrays.

Figure 4:
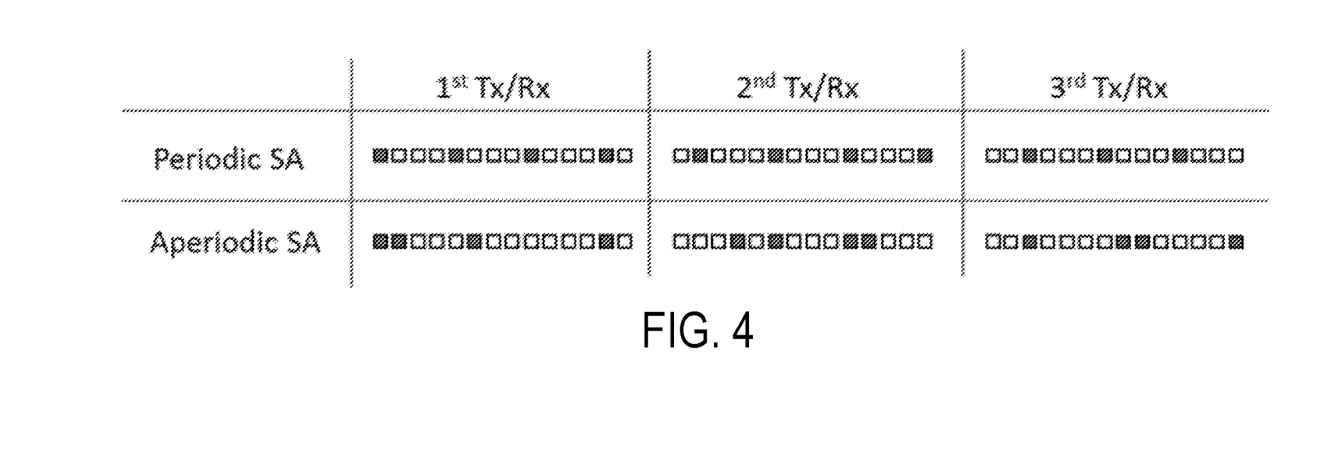
FIG. 4 shows an example classification for different sparse arrays in different transmit/receive events.

Sparse arrays can also be categorized according to whether or not the aperture shape is changed per beam or Tx/Rx event. FIG. 4 shows example of different categories for sparse arrays if the shape is fixed or changed per beam or Tx/Rx event. A Tx beam is the transmission event using a shape of array aperture and a Rx beam is the reception event using a shape of array aperture. Different shapes of array apertures can be used in each beam. In linear arrays or curvilinear arrays, the aperture can be shifted for different Tx/Rx events per beam. Periodic sparse arrays, as shown in the upper row of FIG. 4, can be changed in different Tx/Rx events. Aperiodic or random sparse arrays also can be used for switching the shape of array aperture in different Tx/Rx events, as shown in the bottom row in FIG. 4. The change of array aperture shape can be optimized to find an optimal solution for generating and estimating unacquired and unknown channel data. For different Tx/Rx events, any suitable Tx method used in synthetic transmit aperture, plane wave compounding, and standard Tx focused beamforming can be adopted.

Thus, in some embodiments of the systems and methods described in the present disclosure, a trained machine learning algorithm can be trained to generate the additional ultrasound data associated with empty or inactive channels based on neighboring data in the acquired ultrasound data. In still other embodiments, the trained machine learning algorithm can be trained to generate these additional ultrasound data based on other, additional information.

As one example, additional information can be previously acquired channel data from different or same objects for ultrasound imaging. The objects can be any part or whole of a subject or object, or can be any material. Additional information can be an input of any suitable type that the trained machine learning algorithm can use to generate the additional ultrasound data.

The additional information (e.g., data or other information apart from known and acquired data) can be used to generate additional ultrasound data, which may be empty or unknown data in RF echo channel data, beamforming line data, I/Q data, and image pixel data.

Both existing and additional information can be used to generate the additional ultrasound data.

By using the systems and methods described in the present disclosure, the system size and cost for 2D array ultrasound systems can be reduced without degrading image quality and performance. Normally, ultrasound systems using 2D arrays require a massive number of channels and large volumes of data processing. For instance, M×N channels are typically required for activating M×N 2D array elements while N channels are required for using N elements in a 1D array transducer having N elements. Thus, the size of the front-end system and connection between a 2D array transducer and ultrasound system is significantly increased. Moreover, to process the data acquired from a fully sampled 2D array for volume scanning requires a significant increase in the amount of data acquired for the number of Tx/Rx events. Thus, using the systems and methods described in the present disclosure, a reduced amount of data can be acquired and additional ultrasound data can be generated by the trained machine learning algorithm in order to keep image quality high while reducing the resource and computational burden on the ultrasound system. The amount of acquired data can also be reduced according to how different shapes of an SA aperture are used in different Tx/Rx events. The systems and methods described in the present disclosure can also be utilized for small-scale and hand-held devices that require reduced number of active channels and power consumption.

In some other embodiments, the additional ultrasound data generated by the trained machine learning algorithm correspond to pseudo channel data between two or more existing physical channels. This additional ultrasound data can similarly be used to improve the quality of RF echo channel data, beamforming line data, I/Q data, and image pixels, or at any other stage in the ultrasound signal processing chain. The technique improves quality, for instance, by increasing the fidelity of the lateral data and decreasing the pitch size.

In other embodiments, the additional ultrasound data generated by the trained machine learning algorithm correspond to different positions in synthetic transmit aperture focusing ("STAF") techniques. In STAF, different positions of a source aperture are used for firing ultrasound, and the RF echoes received from different positions are combined for generating retrospective transmission focused fields. As an example, the ultrasound waves, which may be diverged or focused ultrasound waves, are transmitted at the first position of source aperture by using N channels. Next, the ultrasound waves are transmitted at the second position of source aperture by using N channels, then at the third position, and so on. Using the systems and methods described in the present disclosure, instead of firing ultrasound waves at every position, some positions can be skipped (e.g., every other position) to not fire and acquire the RF echo data. Such unacquired data can be referred to as unacquired scan-line data. Then the RF echo data corresponding to these skipped positions can be generated as additional ultrasound data using the systems and methods described in the present disclosure.

In other embodiments, the additional ultrasound data generated by the trained machine learning algorithm correspond to different angles for compounded imaging applications, such as compounded plane wave imaging. Ultrasound waves focused at infinity can be referred to as plane waves. Planes waves with different directivity of main lobes can be used to gather more information about the scattering medium. The process of adding the different angles is called compounding. Coherent compounding techniques add plane waves from different angles, which are acquired within a short time interval so that there is minimal to no loss of coherency in the data. Coherent plane wave compounding uses data from multiple angles to form a single image, which increases the quality of the image, but reduces the frame rate. Thus, by acquiring ultrasound data over fewer angles the frame rate can be increased, but at the expense of reduced image quality. In these examples, the acquired ultrasound data provided in step 102 include data from fewer angles that would be desirable for reconstructing a high quality image. However, the trained machine learning algorithm can be trained to generate additional ultrasound data that includes data from angles not acquired in the initially acquired ultrasound data. As such, higher quality images can be reconstructed with increased frame rate. As one example, the acquired ultrasound data can include data from a zero degree angle and data from an 18 degree angle. Based on these data, the trained machine learning algorithm can generate additional ultrasound data corresponding to data from a 9 degree angle.

Traditional coherent plane wave compounding can sometimes suffer from an axial lobe artifact. Axial lobes present as an artifactual, and unwanted, bright spot that shows up under a bright target in the reconstructed images. These artifacts can result from large pitch size in the array; therefore, reducing the pitch size can reduce these axial lobes. The systems and methods described in the present disclosure can be used to generate additional ultrasound data in conjunction with artificially reducing the pitch size of the ultrasound transducer in order to reduce the size of axial lobes and, therefore, improve image quality. As a result, the performance of a low-end (and low-cost) transducer array can be improved to produce high quality images similar to those attainable with an otherwise costly, high-end probe.

Figure 5:
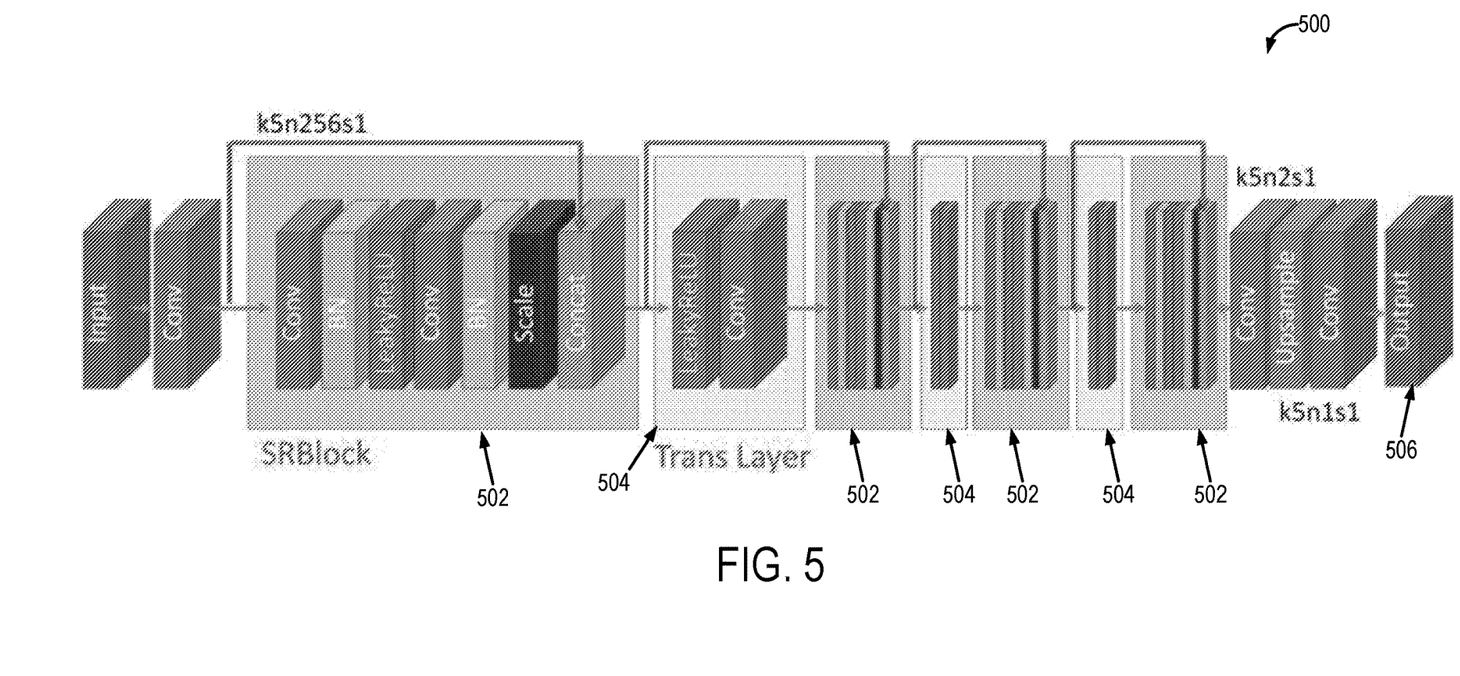
FIG. 5 is an example of a deep learning model that can be used in some embodiments of the present disclosure to generate additional ultrasound data from input ultrasound data.

Referring now to FIG. 5, an example of a deep learning model 500 that can be used to generate additional ultrasound data according to some embodiments of the systems and methods described in the present disclosure is shown. In this example, a convolution neural network ("CNN") is used along with skip connections to concatenate both global and local features of an image. The input to the model is a sparse RF-echo data set, or other suitable ultrasound data set with fewer than desired data, and the output is an RF-echo data set of a desired size (i.e., a concatenation or other combination of the input ultrasound data and the additional ultrasound data).

The deep learning model 500 shown in FIG. 5 includes two repeating blocks: an SR block 502 and a Trans layer 504. The SR block 502 captures local features and merges them with global features. The SR block 502 for this embodiment is made of a convolutional layer and batch normalization with a leaky rectified linear unit ("ReLU") as the activation function. However, any combination of deep learning layers can be used to capture the local features and then merged with the global features using the skip connection. Likewise, activation functions other than a leaky ReLU can be used. An example kernel size of 5×5, with 256 filters and stride size of 1 (k5n256s1) is used in the embodiment shown in FIG. 5; however, the kernel size, number of filters, and stride size can be optimized or otherwise modified according to the dataset to be processed. The number of filters is reduced to 1 before the output layer 506 in order to match the output layer 506. Multiple SR blocks 502 ensure that higher order statistics are captured.

The Trans layer 504 extracts features from the concatenated output of the SR block 502 and the input to the SR block 502. A variety of loss functions can be used for the convergence of the deep learning model 500 shown in FIG. 5, including mean squared error, mean absolute error, peak signal to noise ratio, structural similarity index, and so on.

Figure 6:
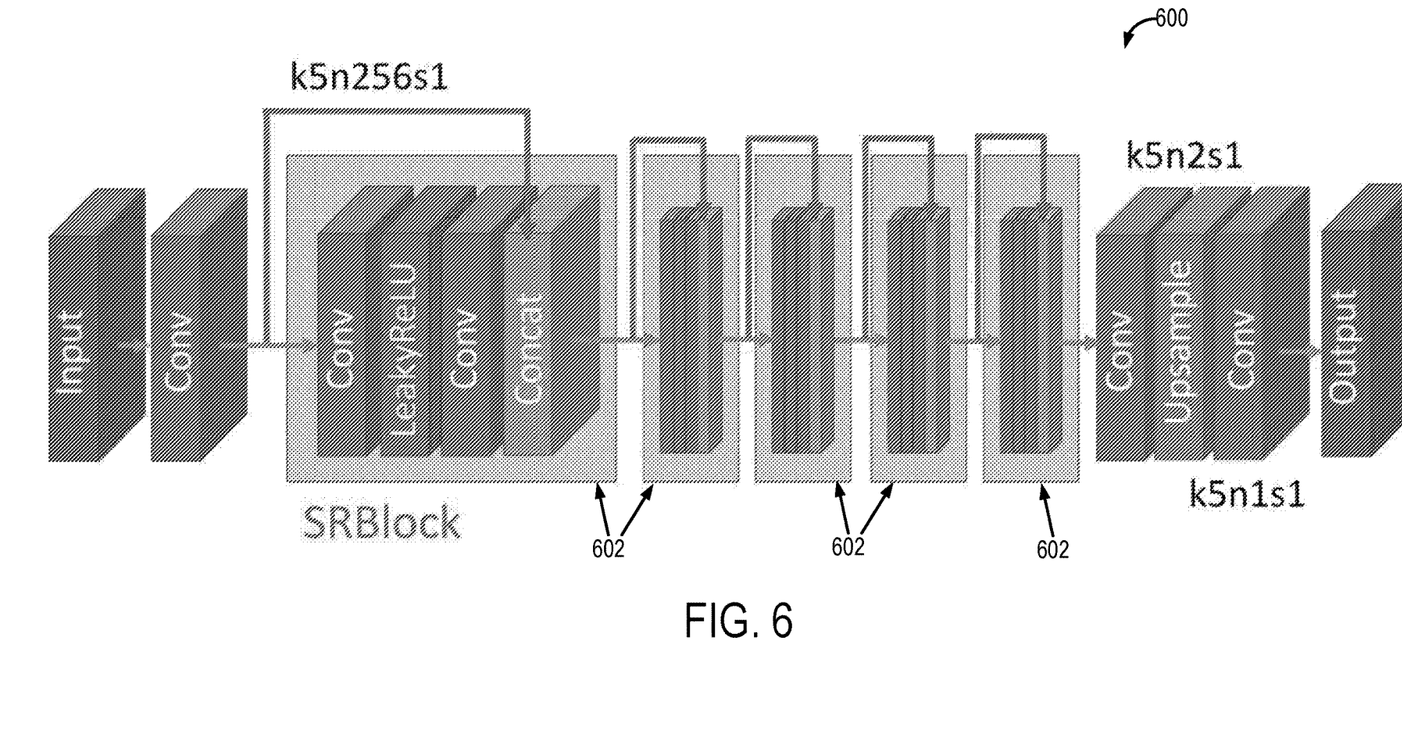
FIG. 6 is an example of a deep learning model having a reduced number of layers to increase the speed of the machine learning algorithm, and which can be used in some embodiments of the present disclosure to generate additional ultrasound data from input ultrasound data.

The computation complexity of the deep learning model shown in FIG. 5 can in some instances be high. In order to reduce the computation complexity, and thus the computation time, the Trans layer 504 can be removed. Referring now to FIG. 6, another example of a deep learning model 600 that can be used to generate additional ultrasound data according to some embodiments of the systems and methods described in the present disclosure is shown. In this example, no Trans layer is used, but an SR block 602 is repeated. In this example, the batch normalization and scaling layers are also removed from the SR block 602, as compared to the example shown in FIG. 5. Any combination of deep learning layers can be used in the SR blocks 602. Likewise, activation functions other than a leaky ReLU can be used. The kernel size, number of filters, and stride size can also be optimized or otherwise modified according to the dataset to be processed. The embodiment shown in FIG. 6 does well in capturing larger signals as compared to smaller signals.

Figure 7:
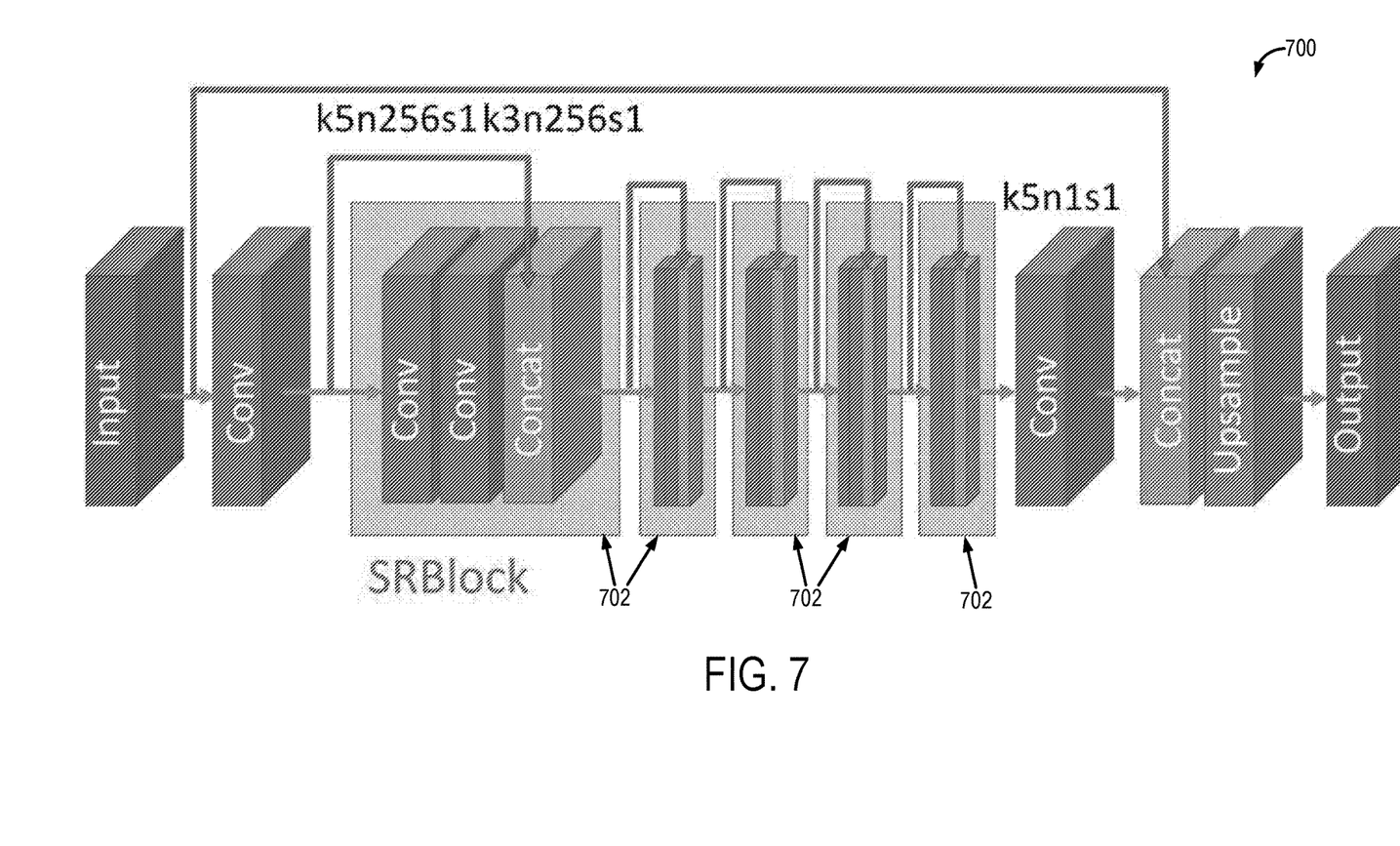
FIG. 7 is an example of a deep learning model having a skip connection between from the input in order to enable improved representation of smaller signals, and which can be used in some embodiments of the present disclosure to generate additional ultrasound data from input ultrasound data.

Referring now to FIG. 7, another example of a deep learning model 700 that can be used to generate additional ultrasound data according to some embodiments of the systems and methods described in the present disclosure is shown. To ensure that smaller signals are also recovered in the output, the deep learning model 700 shown in FIG. 7 uses a skip connection to concatenate the input with the collected features. Any combination of deep learning layers can be used in the SR blocks 702. Likewise, activation functions other than a leaky ReLU can be used. The kernel size, number of filters, and stride size can also be optimized or otherwise modified according to the dataset to be processed.

Figure 8:
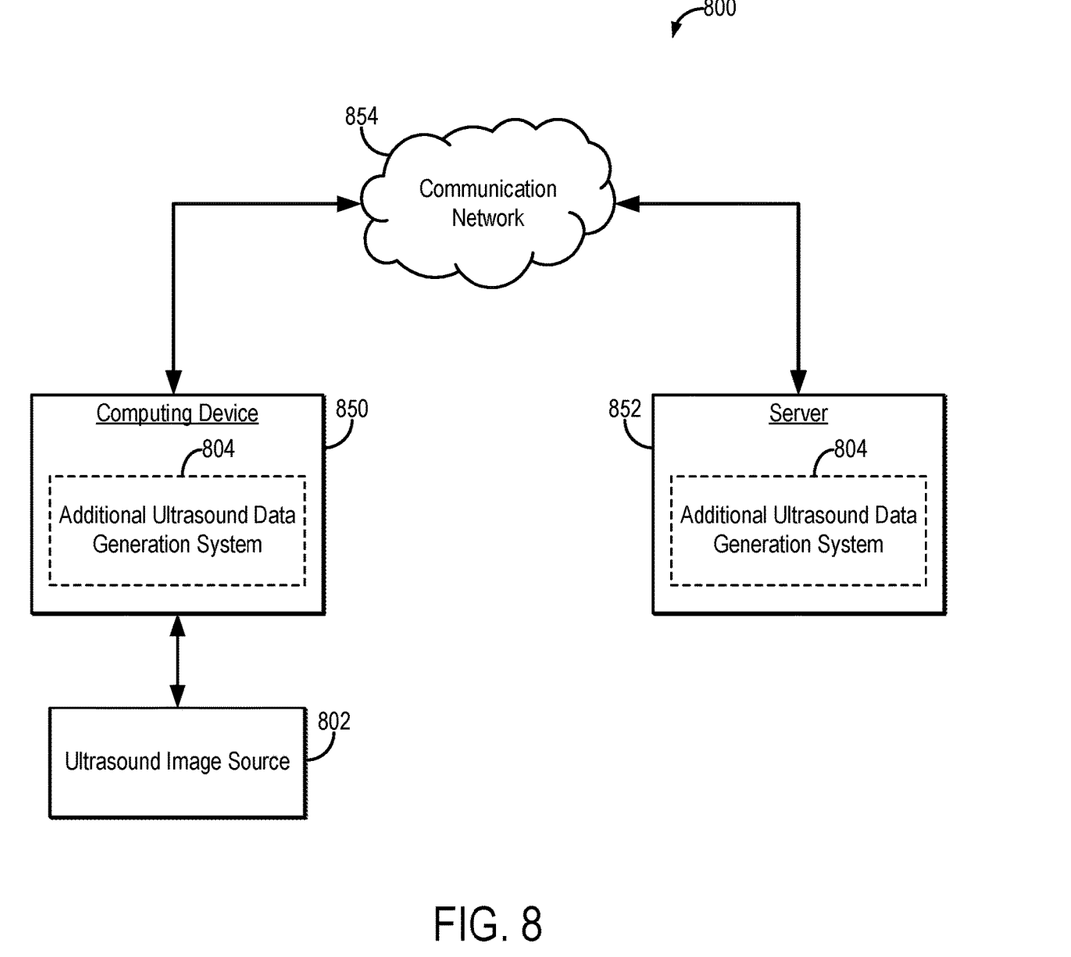
FIG. 8 is a block diagram of an example system that can implement the methods described in the present disclosure.

Referring now to FIG. 8, an example of a system 800 for generating additional ultrasound data from input ultrasound data in accordance with some embodiments of the systems and methods described in the present disclosure is shown. As shown in FIG. 8, a computing device 850 can receive one or more types of ultrasound data from ultrasound image source 802. In some embodiments, computing device 850 can execute at least a portion of an additional ultrasound data generation system 804 to generate additional ultrasound data (e.g., from empty channels, inactive channels, unacquired angles) from ultrasound data received from the ultrasound image source 802.

Additionally or alternatively, in some embodiments, the computing device 850 can communicate information about ultrasound data received from the ultrasound image source 802 to a server 852 over a communication network 854, which can execute at least a portion of the additional ultrasound data generation system 804 to generate additional ultrasound data (e.g., from empty channels, inactive channels, unacquired angles) from ultrasound data received from the ultrasound image source 802. In such embodiments, the server 852 can return information to the computing device 850 (and/or any other suitable computing device) indicative of an output of the additional ultrasound data generation system 804 to generate additional ultrasound data (e.g., from empty channels, inactive channels, unacquired angles) from ultrasound data received from the ultrasound image source 802.

In some embodiments, computing device 850 and/or server 852 can be any suitable computing device or combination of devices, such as a desktop computer, a laptop computer, a smartphone, a tablet computer, a wearable computer, a server computer, a virtual machine being executed by a physical computing device, and so on. As described above, the additional ultrasound data generation system 804 can use one or more trained machine learning algorithms, which may include one or more CNNs, to generate additional ultrasound data, such as data corresponding to empty channels, inactive channels, unacquired angles, and so on. The computing device 850 and/or server 852 can also reconstruct images from ultrasound data, such as the initially acquired ultrasound data, additional ultrasound data, combinations of such data, and so on.

In some embodiments, ultrasound image source 802 can be any suitable source of ultrasound image data, such as an ultrasound machine, another computing device (e.g., a server storing ultrasound image data), and so on. In some embodiments, ultrasound image source 802 can be local to computing device 850. For example, ultrasound image source 802 can be incorporated with computing device 850 (e.g., computing device 850 can be configured as part of a device for capturing, scanning, and/or storing ultrasound images). As another example, ultrasound image source 802 can be connected to computing device 850 by a cable, a direct wireless link, and so on. Additionally or alternatively, in some embodiments, ultrasound image source 802 can be located locally and/or remotely from computing device 850, and can communicate ultrasound data to computing device 850 (and/or server 852) via a communication network (e.g., communication network 854).

In some embodiments, communication network 854 can be any suitable communication network or combination of communication networks. For example, communication network 854 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 8 can each be any suitable communications link or combination of communications links, such as wired links, fiber optic links, Wi-Fi links, Bluetooth links, cellular links, and so on.

Figure 9:
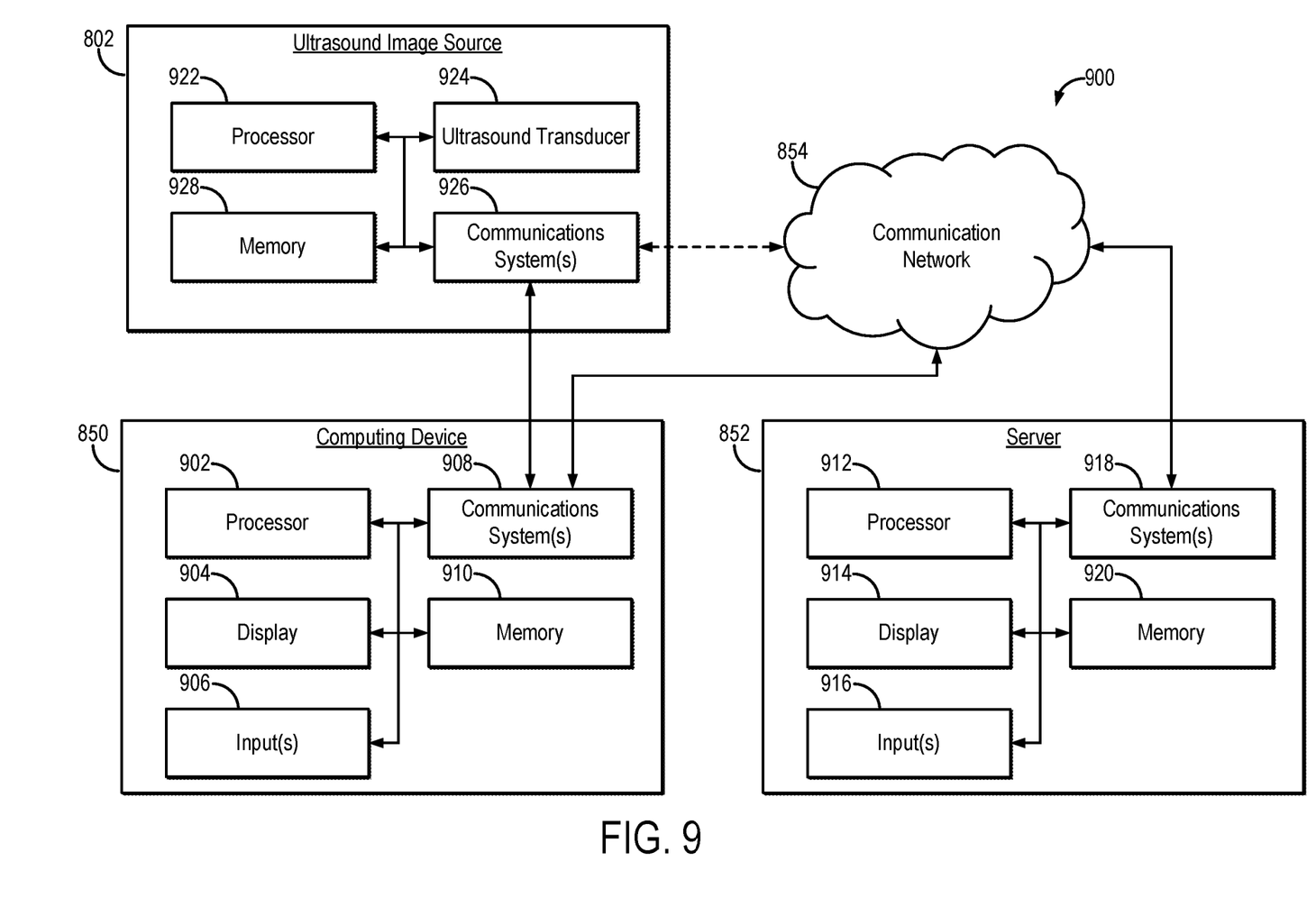
FIG. 9 is a block diagram of example hardware that can implement the system of FIG. 8.

Referring now to FIG. 9, an example of hardware 900 that can be used to implement ultrasound image source 802, computing device 850, and server 854 in accordance with some embodiments of the systems and methods described in the present disclosure is shown. As shown in FIG. 9, in some embodiments, computing device 850 can include a processor 902, a display 904, one or more inputs 906, one or more communication systems 908, and/or memory 910. In some embodiments, processor 902 can be any suitable hardware processor or combination of processors, such as a central processing unit ("CPU"), a graphics processing unit ("GPU"), and so on. In some embodiments, display 904 can include any suitable display devices, such as a computer monitor, a touchscreen, a television, and so on. In some embodiments, inputs 906 can include any suitable input devices and/or sensors that can be used to receive user input, such as a keyboard, a mouse, a touchscreen, a microphone, and so on.

In some embodiments, communications systems 908 can include any suitable hardware, firmware, and/or software for communicating information over communication network 854 and/or any other suitable communication networks. For example, communications systems 908 can include one or more transceivers, one or more communication chips and/or chip sets, and so on. In a more particular example, communications systems 908 can include hardware, firmware and/or software that can be used to establish a Wi-Fi connection, a Bluetooth connection, a cellular connection, an Ethernet connection, and so on.

In some embodiments, memory 910 can include any suitable storage device or devices that can be used to store instructions, values, etc., that can be used, for example, by processor 902 to present content using display 904, to communicate with server 852 via communications system(s) 908, etc. Memory 910 can include any suitable volatile memory, non-volatile memory, storage, or any suitable combination thereof. For example, memory 910 can include RAM, ROM, EEPROM, one or more flash drives, one or more hard disks, one or more solid state drives, one or more optical drives, etc. In some embodiments, memory 910 can have encoded thereon a computer program for controlling operation of computing device 850. In such embodiments, processor 902 can execute at least a portion of the computer program to present content (e.g., ultrasound images, user interfaces, graphics, tables, etc.), receive content from server 852, transmit information to server 852, etc.

In some embodiments, server 852 can include a processor 912, a display 914, one or more inputs 916, one or more communications systems 918, and/or memory 920. In some embodiments, processor 912 can be any suitable hardware processor or combination of processors, such as a CPU, a GPU, etc. In some embodiments, display 914 can include any suitable display devices, such as a computer monitor, a touchscreen, a television, etc. In some embodiments, inputs 916 can include any suitable input devices and/or sensors that can be used to receive user input, such as a keyboard, a mouse, a touchscreen, a microphone, etc.

In some embodiments, communications systems 918 can include any suitable hardware, firmware, and/or software for communicating information over communication network 854 and/or any other suitable communication networks. For example, communications systems 918 can include one or more transceivers, one or more communication chips and/or chip sets, etc. In a more particular example, communications systems 918 can include hardware, firmware and/or software that can be used to establish a Wi-Fi connection, a Bluetooth connection, a cellular connection, an Ethernet connection, etc.

In some embodiments, memory 920 can include any suitable storage device or devices that can be used to store instructions, values, etc., that can be used, for example, by processor 912 to present content using display 914, to communicate with one or more computing devices 850, etc. Memory 920 can include any suitable volatile memory, non-volatile memory, storage, or any suitable combination thereof. For example, memory 920 can include RAM, ROM, EEPROM, one or more flash drives, one or more hard disks, one or more solid state drives, one or more optical drives, etc. In some embodiments, memory 920 can have encoded thereon a server program for controlling operation of server 852. In such embodiments, processor 912 can execute at least a portion of the server program to transmit information and/or content (e.g., generated additional ultrasound data, ultrasound images, a user interface, etc.) to one or more computing devices 850, receive information and/or content from one or more computing devices 850, receive instructions from one or more devices (e.g., a personal computer, a laptop computer, a tablet computer, a smartphone, etc.), etc.

In some embodiments, ultrasound image source 802 can include a processor 922, an ultrasound transducer 924, one or more communications systems 926, and/or memory 928. In some embodiments, processor 922 can be any suitable hardware processor or combination of processors, such as a CPU, a GPU, etc. In some embodiments, ultrasound transducer 924 can be any suitable ultrasound probe configured to generate ultrasound data corresponding to one or more ultrasound imaging modes (e.g., B-mode ultrasound, color Doppler ultrasound, shear wave elastography ultrasound). Additionally or alternatively, in some embodiments, ultrasound transducer 924 can include any suitable hardware, firmware, and/or software for coupling to and/or controlling operations of an ultrasound transducer. In some embodiments, one or more portions of ultrasound transducer 924 can be removable and/or replaceable (e.g., with a transducer that is configured to generate ultrasound data corresponding to a different mode, that is configured to generate ultrasound data with higher or lower resolution, with a transducer that has a different sparse array characteristics, and so on).

Note that, although not shown, ultrasound image source 802 can include any suitable inputs and/or outputs. For example, ultrasound image source 802 can include input devices and/or sensors that can be used to receive user input, such as a keyboard, a mouse, a touchscreen, a microphone, a trackpad, a trackball, etc. As another example, ultrasound image source 802 can include any suitable display devices, such as a computer monitor, a touchscreen, a television, etc., one or more speakers, etc.

In some embodiments, communications systems 926 can include any suitable hardware, firmware, and/or software for communicating information to computing device 850 (and, in some embodiments, over communication network 854 and/or any other suitable communication networks). For example, communications systems 926 can include one or more transceivers, one or more communication chips and/or chip sets, etc. In a more particular example, communications systems 926 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 928 can include any suitable storage device or devices that can be used to store instructions, values, ultrasound data, etc., that can be used, for example, by processor 922 to control ultrasound transducer 924, and/or receive ultrasound data from ultrasound transducer 924; to generate ultrasound images from ultrasound data, generated additional ultrasound data, or combinations thereof; present content (e.g., ultrasound images, a user interface, etc.) using a display; communicate with one or more computing devices 850; and so on. Memory 928 can include any suitable volatile memory, non-volatile memory, storage, or any suitable combination thereof. For example, memory 928 can include RAM, ROM, EEPROM, one or more flash drives, one or more hard disks, one or more solid state drives, one or more optical drives, etc. In some embodiments, memory 928 can have encoded thereon a program for controlling operation of ultrasound image source 802. In such embodiments, processor 922 can execute at least a portion of the program to generate ultrasound images, transmit information and/or content (e.g., ultrasound data) to one or more computing devices 850, receive information and/or content from one or more computing devices 850, receive instructions from one or more devices (e.g., a personal computer, a laptop computer, a tablet computer, a smartphone, etc.), etc.

Figure 10:
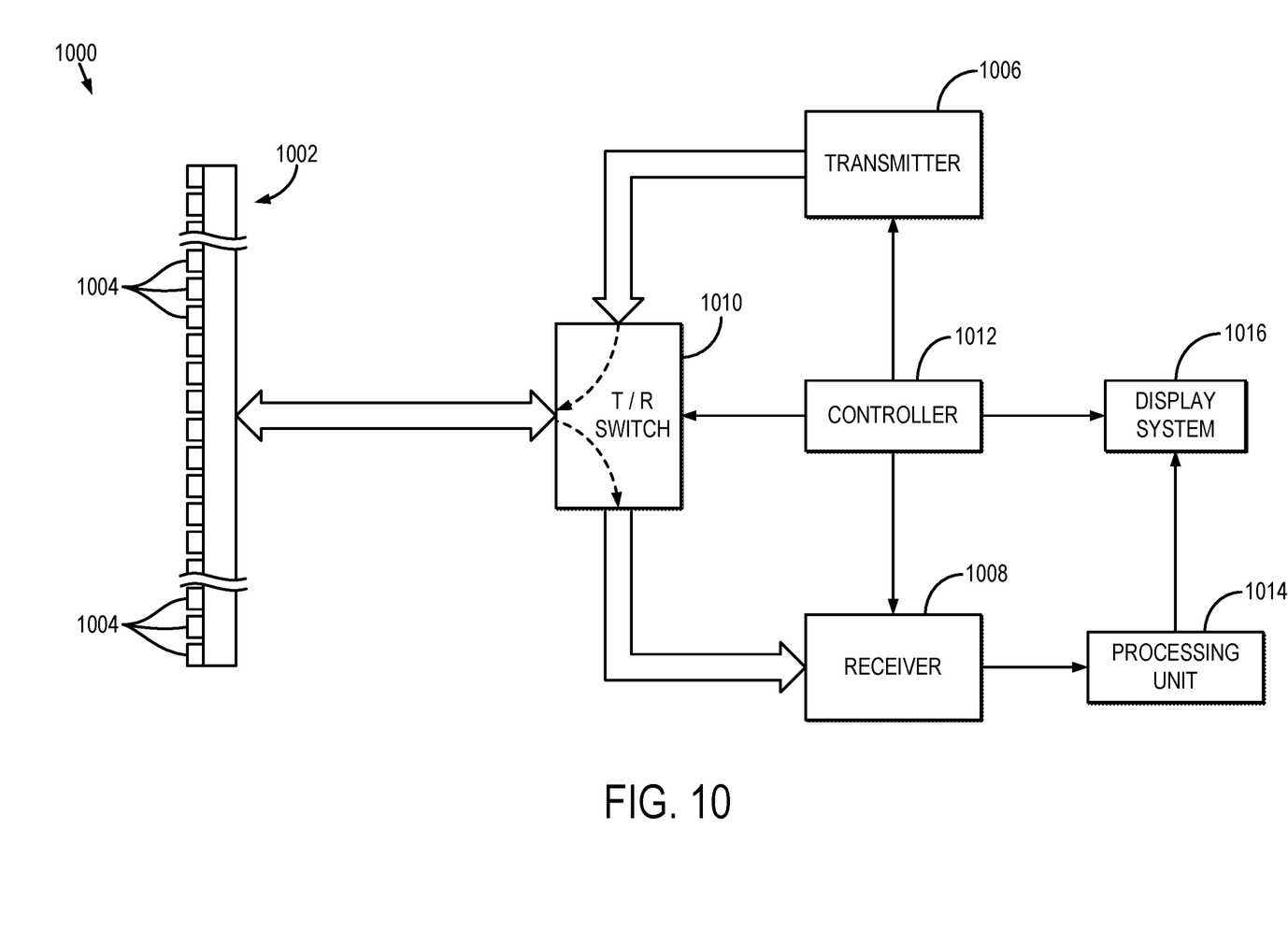
FIG. 10 is an example of an ultrasound system that can implement some embodiments of the systems and methods described in the present disclosure.

FIG. 10 illustrates an example of an ultrasound system 1000 that can implement the methods described in the present disclosure. The ultrasound system 1000 includes a transducer array 1002 that includes a plurality of separately driven transducer elements 1004. The transducer array 1002 can include any suitable ultrasound transducer array, including linear arrays, curved arrays, phased arrays, and so on. Similarly, the transducer array 1002 can include a 1D transducer, a 1.5D transducer, a 1.75D transducer, a 2D transducer, a 3D transducer, and so on.

When energized by a transmitter 1006, a given transducer element 1004 produces a burst of ultrasonic energy. The ultrasonic energy reflected back to the transducer array 1002 (e.g., an echo) from the object or subject under study is converted to an electrical signal (e.g., an echo signal) by each transducer element 1004 and can be applied separately to a receiver 1008 through a set of switches 1010. The transmitter 1006, receiver 1008, and switches 1010 are operated under the control of a controller 1012, which may include one or more processors. As one example, the controller 1012 can include a computer system.

The transmitter 1006 can be programmed to transmit unfocused or focused ultrasound waves. In some configurations, the transmitter 1006 can also be programmed to transmit diverged waves, spherical waves, cylindrical waves, plane waves, or combinations thereof. Furthermore, the transmitter 1006 can be programmed to transmit spatially or temporally encoded pulses.

The receiver 1008 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1006 and the receiver 1008 can be programmed to implement a high frame rate. For instance, a frame rate associated with an acquisition pulse repetition frequency ("PRF") of at least 100 Hz can be implemented. In some configurations, the ultrasound system 1000 can sample and store at least one hundred ensembles of echo signals in the temporal direction.

The controller 1012 can be programmed to implement a selected imaging sequence to acquire ultrasound data. In some embodiments, the controller 1012 receives user inputs defining various factors used in the design of the imaging sequence.

A scan can be performed by setting the switches 1010 to their transmit position, thereby directing the transmitter 1006 to be turned on momentarily to energize transducer elements 1004 during a single transmission event according to the selected imaging sequence. The switches 1010 can then be set to their receive position and the subsequent echo signals produced by the transducer elements 1004 in response to one or more detected echoes are measured and applied to the receiver 1008. The separate echo signals from the transducer elements 1004 can be combined in the receiver 1008 to produce a single echo signal.

The echo signals are communicated to a processing unit 1014, which may be implemented by a hardware processor and memory, to process echo signals or images generated from echo signals. As an example, the processing unit 1014 can generate additional ultrasound data and/or generate ultrasound images using the methods described in the present disclosure. Images produced from the echo signals by the processing unit 1014 can be displayed on a display system 1016.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for reconstructing an image from data acquired with an ultrasound system, comprising:
   (a) accessing with a computer system, ultrasound data acquired from a subject with an ultrasound system, wherein the ultrasound data correspond to one or more data channels of the ultrasound system, wherein each data channel of the ultrasound system corresponds to a transducer element of a transducer array of the ultrasound system;
   (b) generating additional ultrasound data with the computer system by inputting the ultrasound data to a trained machine learning algorithm that is trained to generate additional ultrasound data based on the acquired ultrasound data, generating output as the additional ultrasound data, wherein the additional ultrasound data correspond to data channels of the ultrasound system that were not sampled when acquiring the ultrasound data;
   (c) reconstructing with the computer system, an image from the ultrasound data and the additional ultrasound data, wherein the image depicts the subject from which the ultrasound data were acquired.

2. The method as recited in claim 1, wherein the additional ultrasound data comprise data corresponding to unacquired channel data.

3. The method as recited in claim 1, wherein the additional data comprise data corresponding to unacquired steering angle data.

4. The method as recited in claim 1, wherein the additional data comprise data corresponding to pseudo channel data associated with an arbitrary position on the transducer array.

5. The method as recited in claim 4, wherein the arbitrary position corresponds to a virtual channel between two physical channels.

6. The method as recited in claim 1, wherein the trained machine learning algorithm comprises a deep learning model.

7. The method as recited in claim 6, wherein the deep learning model comprises a plurality of SR blocks.

8. The method as recited in claim 7, wherein each SR block comprises at least one convolutional layer and at least one activation function layer.

9. The method as recited in claim 8, wherein the at least one activation function layer comprises a leaky rectified linear unit (ReLU).

10. The method as recited in claim 8, wherein each SR block further comprises at least one batch normalization layer.

11. The method as recited in claim 7, wherein the deep learning model further comprises a plurality of Trans layers.

12. The method as recited in claim 11, wherein each Trans layer receives an input from one of the plurality of SR blocks.

13. The method as recited in claim 7, wherein each SR block includes a skip connection that concatenates an input to the SR block with an output of the SR block.

14. The method as recited in claim 7, wherein the deep learning model includes a skip connection that concatenates the acquired ultrasound data with an output of the plurality of SR blocks.

15. The method as recited in claim 7, wherein each SR block receives input data, captures local features from the input data, merges the local features with global features in the input data, and generates output as merged local features and global features.

* * * * *